US00PP14348P29

(12) United States Plant Patent
Winters

(10) Patent No.: US PP14,348 P2
(45) Date of Patent: Dec. 9, 2003

(54) PLANT NAMED HIBISCUS 'VULCAN'

(50) Latin Name: *Hibiscus spp.*
Varietal Denomination: Vulcan

(76) Inventor: Harold F. Winters, 10717 Kinloch Rd., Silver Spring, MD (US) 20903

( * ) Notice: Subject to any disclaimer, the term of this patent is extended or adjusted under 35 U.S.C. 154(b) by 0 days.

(21) Appl. No.: 09/514,878

(22) Filed: Feb. 28, 2000

(51) Int. Cl.[7] ..... A01H 5/00
(52) U.S. Cl. ..... Plt./257

(58) Field of Search ..... Plt./257

*Primary Examiner*—Bruce R. Campell
*Assistant Examiner*—Annette H. Para

(57) ABSTRACT

An herbaceous perennial Hibiscus plant named 'Vulcan', of hybrid background, bearing numerous, large, partially sterile flowers of red-purple that remain expanded for at least one full day, and, with strong upright stems that resist lodging and bear large, lobed leaves basally and entire upper leaves of a medium green color. The plants are of ornamental value for the flowers and as plants for landscape plantings. The flowering period extends from mid-summer until frost.

1 Drawing Sheet

The present invention comprises a new and distinct cultivar of Rosemallow Hibiscus spp. hybrids hereinafter referred to by the cultivar name 'Vulcan'.

CROSS-REFERENCES TO RELATED APPLICATIONS

No other plant patent application has been submitted for Hibiscus 'Vulcan' nor for any sibling of 'Vulcan'.

RIGHTS TO THE INVENTION

The present invention was developed entirely on property owned by the applicant using parent plants owned by him and without Federal sponsorship.

BACKGROUND OF THE INVENTION

1. Field of the Invention

The new cultivar is of value for its floral display, produced from mid- to late-July until frost depending upon cultural, environmetal and seasonal conditions, and for the landscape value of the entire plant.

2. Description of Relevant Prior Art

'Vulcan' originated as a seedling selection from the progeny of a cross pollination between (1) an unnamed seedling selection from a breeding line derived by crossing Hibiscus 'Super Clown' with H. 'Annie J. Hemming', and (2) an unnamed seedling selection from a breeding line derived by crossing the seedling selection described in (1) with H. 'Red Midget'. These Hibiscus cultivars, namely H. 'Super Clown', H. 'Annie J. Hemming' and H. 'Red Midget', exhibit characteristics derived from the native American species of Rosemallow Hibiscus, *H. coccineus* (Medicus) Wal., *H. militaris* Cav. and *H. moscheutos* L. (See: Winters, Harold F. *Our Hardy Hibiscus Species as Ornamentals*. Economic Botany, Vol. 24, No. 2, April–June 1970, pp. 155–164). It is not known just how these native species were hybridized to produce the cultivars used in the present breeding experiments. This prior breeding work was done by others, and the cultivars were available in the nursery trade.

The flower color in Hibiscus 'Vulcan' is intermediate between the flower colors of H. 'Annie J. Hemming' and H. 'Red Midget'. In size, the flowers of H. 'Vulcan' are larger than in any of its parent cultivars. In pose, the flowers of H. 'Vulcan' somewhat resemble those of the species *H. militaris* in that the flowers expand their petals widely. The hastate three- to five-lobed leaves of H. 'Vulcan' also resemble those of *H. militaris* in shape. The stiff, upright main stems of H. 'Vulcan' apparently are derived from *H. coccineus*.

SUMMARY OF THE INVENTION

The breeding program which produced Hibiscus 'Vulcan' extended over a period of some 25 years. The pollen parent was an unnamed purplish-red flowered seedling with red eye-zone that had been selected from the progeny of a cross between Hibiscus 'Super Clown' and the semi-dwarf cultivar H. 'Annie J. Hemming'. The seed parent was a seedling selection from a progeny derived from crossing the above pollen parent with the semi-dwarf, dark-red flowered cultivar H. 'Red Midget'. Each generation of seedlings was rigidly screened for the above named characteristics. Only those which most nearly met all standards were selected as parents of succeeding generations. The new plant produced its first flowers in 1995. It was selected for testing and propagation because of the size and color of its flowers, flower durability, production of only a few seed pods, the strong upright stems, and the landscape value of the plant.

Asexual progagation of this new plant by division and cuttings was carried out on property owned by the applicant at Ridgely, Md. To produce cuttings the plants are headed back before they attain full growth. This causes side branches to develop which are removed for cuttings while the tissues are still soft. Under mist propagation the cuttings produce roots in about one month after which they are removed and potted in soil. Propagation by division is done in early spring before the new stem shoots emerge. The plants are lifted from the ground, split into one or two old-stem divisions (from which the new shoots emerge) and replanted in the field.

The asexually propagated progeny, by both methods, exhibit flower and plant characteristics true to those of the parent plant.

BRIEF DESCRIPTION OF THE ILLUSTRATIONS

1. One year divisions of H. 'Vulcan' showing the rigid, upright character of the main stems, the hastate shape of the middle stem leaves and the somewhat dark glabrous eye-zone of the large flowers.

2. Large, widely expanded flower of H. 'Vulcan' showing the gaps between petal bases and the glabrous eye-zone.

BOTANICAL DESCRIPTION OF THE PLANT

A detailed description of the cultivar follows. The color terminology is in accordance with The Royal Horticultural Society Colour Chart (abbreviated by the letters R.H.S) and followed by the color code number or by ordinary American terminology for color:

The Plant

Hibiscus 'Vulcan' is an herbaceous perennial. The stems are killed to the ground each winter but are replaced by new growths each spring. They grow rigidly upright so are less susceptible to lodging during summer storms than are most Rosemallow Hibiscus plants. Apically the stems are branched and more slender than the main stems. With age the plants develop into multiple-stemmed clumps 1.2 to 1.8 meters (4 to 6 feet ) in height, depending upon environmental conditions such as exposure to sunlight, soil moisture and soil fertility. In color the stems are medium green when young but develop an overcast of reddish purple (R.H. S. 186-A) when mature. Stem bases often attain a diameter of 2.5 to 3.0 cm. (one to 1¼ inches).

After several years growth clumps of Hibiscus 'Vulcan' will develop a spread of 1.2 meters (4 feet). The plants are winter hardy in Maryland without protection of any kind. They grow best in a rich, friable, moist soil. The roots radiate from the stem bases and may attain a diameter of 2 cm. (0.75 inches), and a length of about 30 cm. (12 inches).

The Leaves

The lower stem leaves are generally cordate in shape and may be entire or with short side lobes. Proceeding up the stem they become hastate- to lobed-lanceolate in shape. Those just below the flowers may be entire. The leaf apex is acute, the base shallowly cordate. Leaf margins are irregularly dentate. The heavy-textured lower leaves measure as much as 20 cm. (7.0 in.) long and 15 cm. (6.0 in.) wide, those toward the stem apices become progressively smaller and more tender. They are medium- to dark-green (R.H.S. 137C to R.H.S. 137A) in color. The intensity of the green coloring depends upon the nitrogen nutrition of the plant.

Petioles in well grown plants may attain a length of 14 cm. (5.5 in.) and a diameter of about 0.3 cm. (0.12 in.). In color they vary from medium green (R.H.S. 137C) to reddish purple (R.H.S. 186A). This color may also extend along the major veins of the upper leaf surface, depending upon exposure of the leaf to sunlight.

The Flower

In Maryland, Hibiscus 'Vulcan' starts to flower each year in mid- to late-July and continues for about six weeks, depending upon availability of soil moisture. The plants then produce sporadic flowering until frost. The flowers are borne singly in the axils of leaves beginning about mid-way of the stems progressing upward. Each flower if one full days duration and may remain in good condition for a few hours the following morning. The peduncles subtending the flowers measured 7.8 cm (3.1 in.) in length and 0.3 cm (0.12 in) in diameter. The color is dark green (R.H.S. 137A).

Upon anthesis in the early morning the flower petals reflex, then gradually return to nearly right angles to the central axis and remain thus for the life of the flower. When fully expanded the corolla may measure 30 cm. (12 in.) in diameter. Flowers produced later in the season usually are somewhat smaller. The corolla is composed of five slightly oblique broadly orbicular petals, 14 cm. (5.5 in.) long by 15.2 cm. (6.0 in.) at the widest point. The outer entire margins of the petals overlap to form a complete circle, but the petals narrow toward the point of attachment allowing a slight gap between the bases of each two petals. In texture, each petal varies from somewhat cereous (waxy) at the glabrous base to soft and almost membraneous toward the outer edge.

The petals are dark red in color, R.H.S. Red-Purple Group 61B, with slightly darker veins, R.H.S. Red-Purple Group 60A, developing as the flower ages. The base of each petal is slightly darker in color for 2.5 cm. (1.0 in.) R.H.S. Red-Purple Group 59A, the five petal bases thus forming a glabrous eye-zone.

A stout staminal column protrudes from the central petal attachment that measures 7.8 cm. long (3.0 in.). It bears numerous short-stalked yellow stamens along the basal two-thirds then becomes bare for about 2.0 cm. (0.75 in.) before terminating into five stigmatic branches, each terminating in a capitate stigmatic lobe. In color the column shades from light red, R.H.S. Red Purple Group 63A, at the base to bright red, R.H.S Red-Purple Group 61C, at the stigmatic lobes.

The pistil protrudes from the tip of the anther column for 2.0 cm. (0.75 in.) before separating into five styles, each 0.8 cm. (0.32 in.) long. Each style terminates in a circular granular-surfaced disk 2.0 mm. Thick and 4.0 mm. in diameter. Color of the disk is bright red purple, R.H.S. 65A. Prior to branching the pistil measures 2.0 mm. in diameter. The branches (styles) are about 1.0 mm. in diameter.

Each flower is subtended by a clasping calyx that is composed of five broadly ovate, acute, basally connate sepals of a dark green color, R.H.S. 137A. The sepals measure 4.0 cm. (1.5 in.) in length by 3.0 cm. (0.75 in.) at the widest point. Connate for half their length, the sepals form a structure that clasps the ovary which is entirely enclosed at time of flowering, but develops into a slightly five-lobed, ovoid, acute tipped capsule that measures 2 cm. (0.75 in.) wide by 2.5 cm. (1.0 in.) long. However, Hibiscus 'Vulcan' is almost sterile. A few of the ovaries may mature into capsules late in the season.

The calyx in turn is subtended by a whorl of 10 to 13 (usually 12) awl-shaped clasping bracts of dark green (R.H.S. 137A) color. The slender bracts vary from 2.0 to 4.0 mm. in width at the base and taper to a thread-like apex. In length the bracts vary from 3.0 to 4.0 cm. (1.34 to 1.5 in.).

I claim:

1. A new and distinctive cultivar of Rosemallow Hibiscus plant named 'Vulcan', substantially as herein shown and described, having dark reddish purple flowers of unusually large size and lasting qualities unusaul for these plants, a plant suitable for lanscape use with showy flowers that blooms from midsummer until frost in the fall.

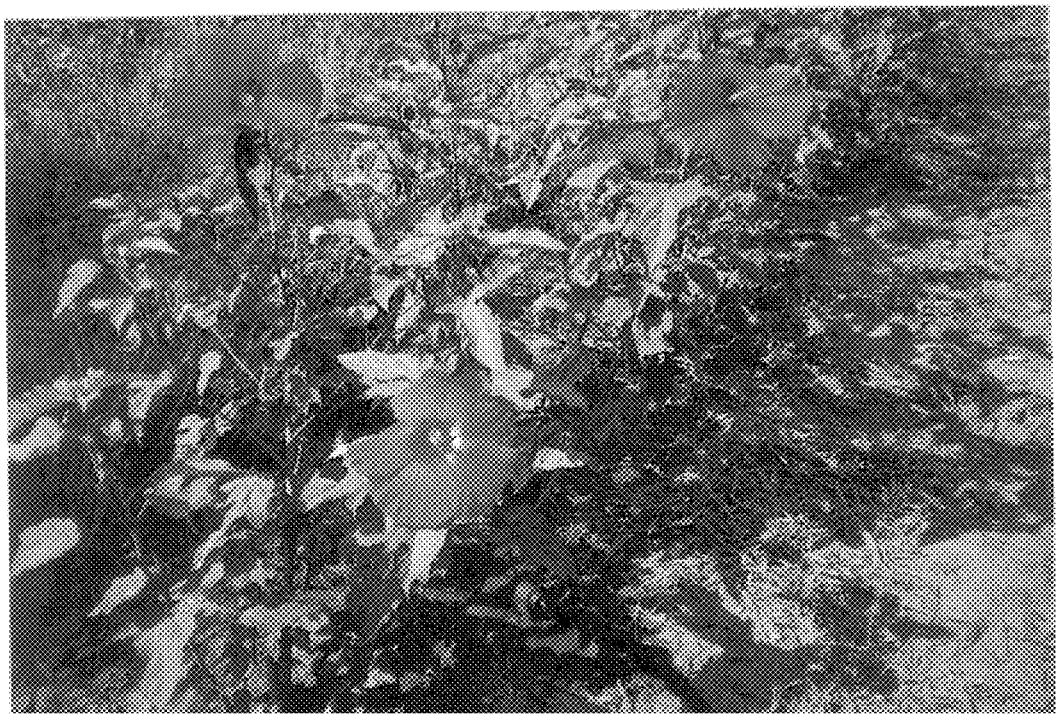
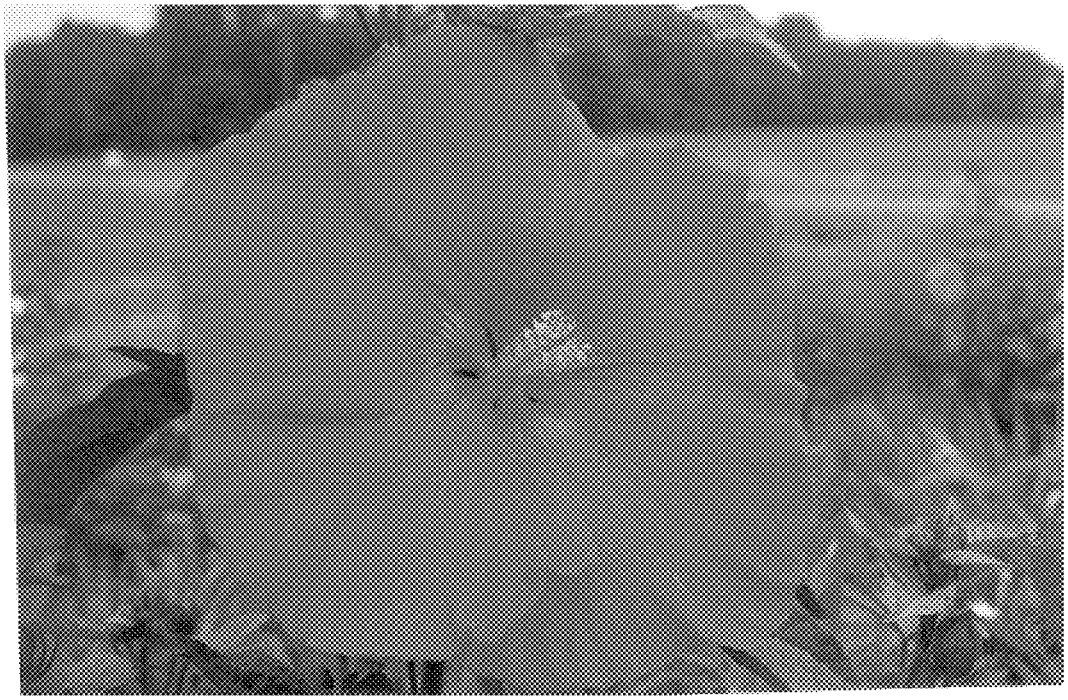

* * * * *